US012721803B2

(12) United States Patent
Pioffet et al.

(10) Patent No.: US 12,721,803 B2
(45) Date of Patent: Sep. 1, 2026

(54) COMPOSITION WITH NON-SILICONE ELASTOMER AND PASTY FATTY SUBSTANCE

(71) Applicant: L V M H RECHERCHE, Saint-Jean de Braye (FR)

(72) Inventors: Corinne Pioffet, Saint Jean de Braye (FR); Amandine Duvert, Saint Jean de Braye (FR); Chantal Kurfurst, Saint Jean de Braye (FR); Marie Hervé-Berdys, Saint Jean de Braye (FR)

(73) Assignee: LVMH RECHERCHE, Saint-Jean de Braye (FR)

( * ) Notice: Subject to any disclaimer, the term of this patent is extended or adjusted under 35 U.S.C. 154(b) by 411 days.

(21) Appl. No.: 18/265,926

(22) PCT Filed: Dec. 9, 2021

(86) PCT No.: PCT/FR2021/052266

§ 371 (c)(1),
(2) Date: Jun. 7, 2023

(87) PCT Pub. No.: WO2022/123184

PCT Pub. Date: Jun. 16, 2022

(65) Prior Publication Data

US 2024/0041749 A1 Feb. 8, 2024

(30) Foreign Application Priority Data

Dec. 11, 2020 (FR) ...................................... 2013052

(51) Int. Cl.

| | |
|---|---|
| ***A61K 8/37*** | (2006.01) |
| ***A61G 1/06*** | (2006.01) |
| ***A61K 8/85*** | (2006.01) |
| ***A61K 8/87*** | (2006.01) |

(52) U.S. Cl.

CPC ................. *A61K 8/87* (2013.01); *A61G 1/06* (2013.01); *A61K 8/37* (2013.01); *A61K 8/85* (2013.01)

(58) Field of Classification Search

None

See application file for complete search history.

(56) References Cited

U.S. PATENT DOCUMENTS

| | | | | |
|---|---|---|---|---|
| 5,707,612 A * | 1/1998 | Zofchak | A61Q 5/12 | 514/846 |
| 2008/0171005 A1 | 7/2008 | Jacques et al. | | |
| 2009/0232752 A1* | 9/2009 | Carson | A61Q 17/04 | 8/405 |
| 2012/0138078 A1* | 6/2012 | Ricard | A61Q 1/02 | 132/200 |
| 2015/0150780 A1* | 6/2015 | Shimizu | A61Q 1/06 | 424/401 |
| 2020/0109231 A1* | 4/2020 | Dolatkhani | C08G 18/36 | |
| 2021/0059924 A1* | 3/2021 | Croom | A61K 8/85 | |

FOREIGN PATENT DOCUMENTS

| | | |
|---|---|---|
| EP | 1498103 B1 | 3/2009 |
| FR | 2949974 A1 | 3/2011 |
| FR | 3092996 A1 | 8/2020 |
| JP | 2015147818 A | 8/2015 |

OTHER PUBLICATIONS

*Moisture Renew Lipstick SPF 20*, Mintel, http://www.gnpd.com (Dec. 2013).

International Search Report issued in PCT Application No. PCT/FR2021/052266, mailed on Mar. 5, 2022.

*Sun Care Technologies, Ease of Use Solutions for Improving Sensory Aesthetics, Durabiltiy and SPF Efficiency*, Grant Industries 1-12 (Jan. 1, 2016).

* cited by examiner

*Primary Examiner* — Susan T Tran

(74) *Attorney, Agent, or Firm* — Panitch Schwarze Belisario & Nadel LLP; Erin M. Dunston

(57) ABSTRACT

The present invention relates to a cosmetic composition, which is preferably solid, comprising, in a physiologically acceptable medium: —a crosslinked polyurethane elastomer gel comprising a single crosslinked polyurethane elastomer (copolymer) or a mixture of at least two crosslinked polyurethane elastomers (copolymers), wherein said copolymer or said mixture of copolymers is obtained from a prepolymer having at least two hydroxyl groups and from a (poly) isocyanate and at least one solvent, in particular from a carboxylic acid dimer or trimer, from at least one polyol and from a diisocyanate, and —one or more pasty fatty substances chosen from the group consisting of (i) esters of polyol(s) and of a fatty acid dimer diacid, or of an ester thereof, (ii) hydrogenated castor oil esters, (iii) glycerol oligomer esters, in particular digylcerol esters, (iv) and mixtures thereof.

19 Claims, No Drawings

COMPOSITION WITH NON-SILICONE ELASTOMER AND PASTY FATTY SUBSTANCE

CROSS-REFERENCE TO RELATED APPLICATIONS

This application is a U.S. National Stage Application pursuant to 35 U.S.C. § 371 of International Patent Application PCT/FR2021/052266, filed on Dec. 9, 2021, and published as WO 2022/123184 on Jun. 16, 2022, which claims priority to French Patent Application FR2013052, filed on Dec. 11, 2020, all of which are incorporated herein by reference in their entireties for all purposes.

FIELD OF THE INVENTION

The present invention relates to the cosmetic field and in particular to compositions comprising a non-silicone elastomer and a particular pasty fatty substance. The non-silicone elastomer is preferably biobased and the composition is preferably a solid lip composition.

STATE OF THE ART

Silicone elastomers are widely used in cosmetics due to their ability to provide sensoriality and mattness to the care and make-up products in which they are used.

However, they have the disadvantage of a silicone chemistry that the consumer abandons in favor of more natural, biodegradable products.

There is still a need to develop new compositions with ingredients of natural or biobased origin, as an alternative to silicone ingredients, but without compromising the stability (texture) of the composition and its sensorial and matte properties on application.

The present invention meets this need by using, in a preferably solid composition, a non-silicone elastomer providing good sensoriality and velvetiness on application and a particular pasty fatty substance. The non-silicone elastomer and the pasty fatty substance are preferably biobased.

This association makes it possible to obtain a homogeneous composition with a very high natural origin and having a sought-after cosmetic attraction: melting, comfort, softness, gummy sensation with a luminous matte make-up finish, a gummed and homogeneous effect on the keratinous materials and in particular the lips.

DISCLOSURE OF THE INVENTION

A first aspect of the invention is therefore a cosmetic composition, preferably solid, comprising, in a physiologically acceptable medium:

a cross-linked polyurethane elastomer gel comprising a single crosslinked polyurethane elastomer (copolymer) or a mixture of at least two crosslinked polyurethane elastomers (copolymers), said copolymer or said mixture of copolymers being obtained from a prepolymer having at least two hydroxyl groups and a (poly) isocyanate and at least one solvent, in particular from a carboxylic acid dimer or trimer, at least one polyol and a diisocyanate, and one or more pasty fatty substances selected from the group consisting of (i) esters of polyol(s) and fatty acid diacid dimer, or an ester thereof (ii) hydrogenated castor oil esters, (iii) oligomeric esters of glycerol, in particular esters of diglycerol, (iv) and mixtures thereof.

According to a particular embodiment, the composition will further comprise at least one ingredient selected from oils, waxes, butters and mixtures thereof.

According to a particular and preferred embodiment, the composition further comprises at least one filler, in particular a mineral filler, preferably still a silica.

Preferably, the composition according to the invention comprises at least 70%, 80%, 90% or even at least 95% by weight of biobased ingredients.

The invention also relates to a cosmetic method comprising a cosmetic method for caring for and/or making up keratinous materials, in particular the skin and/or the lips and preferably the lips, characterized in that it comprises the application to the said keratinous materials and preferably the lips of a composition according to the invention.

DETAILED DESCRIPTION OF THE INVENTION

A first aspect of the invention is therefore a cosmetic composition, preferably solid, comprising, in a physiologically acceptable medium:

a cross-linked polyurethane elastomer gel comprising a single crosslinked polyurethane elastomer (copolymer) or a mixture of at least two crosslinked polyurethane elastomers (copolymers), said copolymer or said mixture of copolymers being obtained from a prepolymer having at least two hydroxyl groups and a (poly) isocyanate and at least one solvent, in particular from a carboxylic acid dimer or trimer, at least one polyol and a diisocyanate, and one or more pasty fatty substances selected from the group consisting of (i) esters of polyol(s) and fatty acid diacid dimer, or an ester thereof (ii) hydrogenated castor oil esters, (iii) oligomeric esters of glycerol, in particular esters of diglycerol, (iv) and mixtures thereof.

According to a particular and preferred embodiment, the composition of the invention is in solid form.

By “solid” is meant a composition having, at 20° C. and atmospheric pressure (1 atm=105 Pa), a hardness greater than 0.5 N, preferably greater than 1.5 N, the said hardness preferably being measured with the aid of a texturometer provided with a hemispherical base of diameter 11.6 mm.

According to a particular and preferred embodiment, the composition of the invention is an anhydrous composition.

By ‘anhydrous’ is meant in particular that water is preferably not intentionally added to the compositions but may be present in the various compounds used in the compositions in trace amounts. In particular, the composition according to the invention comprises less than 4% by weight of water, preferably less than 3%, more preferably less than 2%, even more preferably less than 1%, even more preferably less than 0.5% by weight of water, based on the total weight of said composition, or is even completely free of water.

Advantageously, the ingredients present in the composition of the invention are biobased ingredients.

According to this invention, ‘biobased’ ingredients are ingredients obtained essentially from materials of natural origin. As defined by the ADEME (Agency for Ecological Transition), biobased products are non-food industrial products obtained from renewable raw materials derived from biomass (plants for example).

Thus, according to a particular and preferred embodiment, the composition will comprise at least 70% by weight of biobased ingredients, in particular at least 80%, 90% or even at least 95% by weight of biobased compounds.

Advantageously, the composition of the invention contains less than 5%, preferably less than 1% of silicone compounds. It is preferably free thereof. By silicone compound is meant a molecule comprising at least one silicon atom. The composition is preferably free of a compound chosen from crosslinked silicone polymers such as silicone elastomers, silicone resins, silicone surfactants, silicone gums, cyclic silicones of a volatile nature, and phenylated silicone oils and dimethicones.

Non-Silicone Elastomer (Copolymer According to the Invention)

The term 'non-silicone elastomer' or 'cross-linked polyurethane elastomer' or 'copolymer' of the invention is used interchangeably.

By 'elastomer' is generally meant a cross-linked polymer having elastic properties.

The cross-linked polyurethane elastomer is in particular in gel form, wherein the cross-linked polyurethane elastomer is dispersed in at least one solvent. The elastomer gel may comprise one or more crosslinked polyurethane elastomers.

Preferably the polyurethane elastomer(s) is/are micronized (particle size from 1 to 100 microns, preferably 1 to 60 microns in diameter).

The cross-linked polyurethane elastomer or copolymer of the invention may consist of a single cross-linked polyurethane elastomer (copolymer) or a mixture of at least two cross-linked polyurethane elastomers (copolymers), the copolymer or the mixture of copolymers being obtained from a prepolymer having at least two hydroxyl groups and a (poly)isocyanate and at least one solvent, in particular from a dimer or trimer of a carboxylic acid, preferably of C16-C20, a polyol and a diisocyanate.

Thus, the crosslinked polyurethane elastomer gel or copolymer used in the invention may consist of a single cross-linked polyurethane elastomer (copolymer) or a mixture of at least two crosslinked polyurethane elastomers (copolymers), the elastomer (copolymer) or mixture of elastomers (copolymers) being obtained by reacting a (poly)isocyanate with a prepolymer having at least two hydroxyl groups and a cosmetic solvent under conditions to form the crosslinked polyurethane elastomer. In particular, a urethanization reaction catalyst is used, such as a bismuth or zinc catalyst.

The crosslinked polyurethane elastomer or copolymer of the invention is advantageously biobased, i.e., obtained from raw materials of natural origin (85%, better 90%, even 95% biobased). Thus, according to a preferred embodiment, the prepolymer, the (poly)isocyanate and the cosmetic solvent are more than 85%, or even more than 95%, of natural (e.g., vegetable) origin.

Pre-Polymers

According to a particular embodiment, the prepolymer having at least two hydroxyl groups is a copolymer of a carboxylic acid dimer or trimer, and a polyol.

Examples of pre-polymers include copolymers of a carboxylic acid dimer or trimer, preferably C16-C20, and a polyol.

Examples are cited in the application published as WO202141046 on behalf of Grant Industries Inc.

The carboxylic acid may comprise a linear carbon chain with at least one carbon-carbon double bond, such as an unsaturated fatty acid.

Preferably, the carboxylic acid is a dimer of C12-C18 fatty acids, in particular dilinoleic acid.

The polyol may be saturated or unsaturated, may comprise two or three —OH functions, and optionally comprise other functions such as one or more ester functions. The polyol is for example an aliphatic diol comprising 2 to 8 carbon atoms, in particular 3 or 4 carbon atoms, such as propanediol or butanediol. The polyol can also be a fatty acid triglyceride comprising at least two —OH groups, for example ricinoleic acid triglyceride, or a natural plant source containing it such as castor oil.

Thus, according to a particular embodiment, the polyol is selected from the group consisting of an aliphatic diol comprising 2 to 8 carbon atoms, such as 1,2 ethanediol, propanediols such as 1,2 propanediol, 1,3 propanediol, butanediol, pentanediol, caprylyl glycol, preferably propanediols and butanediol; a fatty acid triglyceride comprising at least two —OH groups, such as ricinoleic acid triglyceride or a vegetable source containing it, such as castor oil.

According to a particular embodiment, the pre-polymer is a dilinoleic acid and propanediol copolymer (DAPD) or a dilinoleic acid and butanediol copolymer (DABP).

(Pol)Isocyanates (Poly)isocyanates are compounds containing an isocyanate group (—NCO). They react with hydroxyl group containing prepolymers to produce polyurethane polymers. The (poly)isocyanate is advantageously a diisocyanate, preferably an aliphatic diisocyanate which may contain 5 or 6 carbon atoms (in its main chain or cycle). The diisocyanate may be linear or cyclic.

Thus, according to a particular embodiment, the (poly) isocyanate is a diisocyanate, in particular an aliphatic diisocyanate that may contain 5 to 6 carbon atoms, preferably selected from 1,6-hexamethylene diisocyanate (HDI), 1,5-pentamethylene diisocyanate (PDI) or isophorone diisocyanate (IPDI).

A preferred (poly)isocyanate is 1,5-pentamethylene diisocyanate trimer.

According to a particular embodiment of the invention:

- the prepolymer having at least two hydroxyl groups is a copolymer of a carboxylic acid dimer or trimer, and a polyol, in particular a C12-C18 fatty acid dimer, preferably dilinoleic acid and a polyol selected from the group consisting of an aliphatic diol having 2 to 8 carbon atoms, such as 1,2-ethanediol, propanediols such as 1,2-propanediol, 1,3-propanediol, butanediol, pentanediol, caprylyl glycol, preferably propanediols and butanediol; a fatty acid triglyceride comprising at least two —OH groups, such as ricinoleic acid triglyceride or a vegetable source containing it, such as castor oil, and in that
- the (poly)isocyanate is a diisocyanate, in particular an aliphatic diisocyanate which may contain 5 to 6 carbon atoms, preferably selected from 1,6-hexamethylene diisocyanate (HDI), 1,5-pentamethylene diisocyanate (PDI) or isophorone diisocyanate (IPDI).

Cosmetic Solvent

As cosmetic solvents used in the synthesis of the crosslinked polyurethane elastomer and/or the formation of the crosslinked polyurethane elastomer gel, esters, ethers, alkanes and mixtures thereof may be mentioned. According to a particular embodiment, one may use: triglycerides of vegetable origin such as glycerol trihexanoate, glycerol triheptanoate (triheptanoin), glycerol trioctanoate, cococaprylate/caprate, C9-C22 alkanes such as undecane, tridecane; esters of natural origin and mixtures thereof, preferably glycerol triheptanoate (triheptanoin), coco-caprylate/caprate, C9-C22 alkanes, esters of natural origin and mixtures thereof.

Thus, according to a particular embodiment, the polyurethane elastomer gel or copolymer of the invention comprises at least one solvent selected from the group consisting of triglycerides of vegetable origin such as glycerol trihexanoate, glycerol triheptanoate (triheptanoin), glycerol trioctanoate, coco-caprylate/caprate, C9-C22 alkanes such as undecane, tridecane; naturally occurring esters and mixtures thereof, preferably glycerol triheptanoate (triheptanoin), coco-caprylate/caprate, C9-C22 alkanes, esters of natural origin and mixtures thereof.

Crosslinked polyurethane elastomers suitable for use according to the invention are described in the application published as WO202141046 on behalf of Grant Industries Inc.

The preparation of a crosslinked polyurethane elastomer and subsequent formation of a crosslinked polyurethane elastomer gel as used according to the invention may include the following steps:

- Reacting a biobased prepolymer with a biobased (poly) isocyanate using a urethanization reaction catalyst such as a bismuth catalyst at a suitable and controlled temperature, e.g., 20° C. to 100° C., in a reaction medium comprising a biobased solvent or a mixture of preferably biobased solvents to form the crosslinked polyurethane elastomer; alternatively, the formation of the crosslinked polyurethane elastomer can be carried out without stirring, at room temperature, for about 24 hours;
- Forming a concentrated elastomer gel as a dispersion by micronizing said cross-linked polyurethane elastomer to a particle size of preferably 1 to 100 microns and optionally adding a cosmetic solvent before or after the micronization step;
- The concentrated elastomer can then optionally be diluted with a secondary solvent, volatile or non-volatile, to achieve the desired viscosity of the crosslinked polyurethane elastomer gel.

Thus, according to a particular embodiment, the cross-linked polyurethane elastomer or copolymer of the invention can be obtained by a first step of preparation of the prepolymer (copolymerization of the C16-C20 carboxylic acid dimer or trimer and the polyol, the polyol being an aliphatic diol comprising 3 or 4 carbon atoms, preferably a linear diol), followed by a second step of reaction of the prepolymer with the (poly)isocyanate consisting in adding the diisocyanate. The carboxylic acid may comprise a linear carbon chain with at least one carbon-carbon double bond, such as an unsaturated fatty acid. The diisocyanate is preferably an aliphatic diisocyanate that may contain 5 or 6 carbon atoms. The diisocyanate may be linear or cyclic. It can be 1,6-hexamethylene diisocyanate (HDI), 1,5-pentamethylene diisocyanate (PDI) or isophorone diisocyanate (IPDI).

According to a particular embodiment, the pre-polymer, which contains 2 hydroxyl groups, represents a content ranging from 5 to 25% by weight of the crosslinked polyurethane elastomer. The preferably biobased (poly)isocyanate contains from 15 to 38%, or from 15 to 28% of —NCO group. The total molar ratio of the —NCO groups of the isocyanate to the OH groups of the polyol can range from 2:1 to 1:2, and is preferably 1:1.

The cosmetic solvent(s) content will generally be from 70 to 95% by weight based on the weight of the crosslinked polyurethane elastomer.

The catalyst content may be from 0.1 to 2.5% by weight.

The crosslinked polyurethane elastomer gel or copolymer of the invention may comprise a crosslinked polyurethane elastomer or a mixture of crosslinked polyurethane elastomers.

According to a particular embodiment, the crosslinked polyurethane elastomer gel used in the compositions according to the invention may comprise from 5 to 30% by weight, in particular from 5 to 17% by weight of crosslinked polyurethane elastomer(s) active material, and from 70 to 95% by weight, in particular from 83 to 95% by weight of solvent(s).

According to a particular embodiment, the crosslinked polyurethane elastomer gel used according to the invention is the crosslinked polyurethane elastomer gel prepared in Example 6 or Example 9 of Grant Industries Inc. application WO202141046. The pre-polymer is a copolymer of C8 dimeric acid and 1,3 propanediol (DAPD) or 1,4 butanediol (DABD), the polyisocyanate is pentylene diisocyanate trimer (PDT), the catalyst is bismuth neodecanoate, and the solvent is a mixture of coconut caprylate/caprate and glycerol triheptanoate.

The concentrated gel is then formed by micronizing said cross-linked polyurethane elastomer and adding glycerol triheptanoate. The concentrated gel is then diluted with the addition of C9-C12 alkanes (Vegelight 1214).

Such cross-linked polyurethane elastomer gels are marketed under the name Gransense™ by Grant Industries.

According to a particular embodiment, the prepolymer is a reaction product of a diol and a dimer acid, in particular a dilinoleic acid and propanediol or butanediol and the (poly) isocyanate is a 1,5-pentamethylene diisocyanate trimer.

Thus, according to a particular embodiment, the cross-linked polyurethane elastomer or copolymer or one of the copolymers in the mixture is obtained from dilinoleic acid, propanediol or butanediol and pentamethylene diisocyanate. This cross-linked polyurethane elastomer or copolymer of the invention may be termed a non-silicone elastomer of polyester nature and have the INCI name: polyurethane-10 Elastomer or polyurethane-100 Elastomer.

The following are some of the trade references for Grant Industries Inc.:

- GRANSENSE TC-11X by INCI name Coco-Caprylate/Caprate (and) Triheptanoin (and) Polyurethane-10 Elastomer; and
- GRANSENSE TC-8X by INCI name Coco-Caprylate/Caprate (and) Triheptanoin (and) C9-12 Alkane (and) Polyurethane-100 Elastomer.

According to another particular embodiment, the cross-linked polyurethane elastomer gel or copolymer of the invention comprises a mixture of at least two cross-linked polyurethane elastomers, said mixture being obtained from prepolymers of dilinoleic acid/polyols and isophorone diisocyanate, the two polyols being butanediol and castor oil.

Thus, according to another particular and preferred embodiment, the composition comprises a blend of at least two crosslinked polyurethane elastomers or copolymers of the invention, said blend being obtained from prepolymers of dilinoleic acid/two polyols and isophorone diisocyanate, the two polyols being butanediol and castor oil. For example, the blend contains a first copolymer obtained from dilinoleic acid and butanediol, and a second copolymer obtained from isophorone diisocyanate and castor oil. The mixture of these two elastomers or copolymers may have as INCI names:

Triheptanoin (and) Coco-Caprylate/Caprate (and) Dilinoleic Acid/Butanediol Copolymer (and) Castor Oil/IPDI Copolymer Elastomer, or Coco-Caprylate/Caprate (and) Triheptanoin (and) C9-12 Alkane (and) Dilinoleic Acid/Butanediol Copolymer (and) Castor Oil/IPDI Copolymer Elastomer.

The following are some of the trade references for Grant Industries Inc.:

GRANSENSE TC-18-X-C by INCI name: Coco-Caprylate/Caprate (and) Triheptanoin (and) C9-12 Alkane (and) Dilinoleic Acid/Butanediol Copolymer (and) Castor Oil/IPDI Copolymer Elastomer GRANSENSE TC-21-X-C by INCI name: Triheptanoin (and) Coco-Caprylate/Caprate (and) Dilinoleic Acid/Butanediol Copolymer (and) Castor Oil/IPDI Copolymer Elastomer GRANSENSE TC-21X-SBC by INCI name: Triheptanoin (and) Coco-caprylate/caprate (and) Dilinoleic Acid/Butanediol Copolymer (and) Castor Oil/IPDI Copolymer Elastomer (and) Butyrospermum Parkii (Shea Butter).

The cross-linked polyurethane elastomer or copolymer of the invention (alone or a mixture of two elastomers or copolymers) according to the invention will generally be present in the composition in a total raw material content ranging from 5% to 60% by weight, in particular from 10% to 50% and in particular from 15 to 40% by weight based on the total weight of the composition.

The cross-linked polyurethane elastomer or copolymer of the invention (alone or a mixture of two copolymers) according to the invention will generally be present in the composition in a total (active) dry matter content ranging from 0.5% to 5% by weight, in particular from 1% to 3% and in particular from 2 to 3% by weight relative to the total weight of the composition.

Pasty Fatty Substance

"Pasty fatty compound" or "pasty compound" or "pasty fatty substance" refers to a non-crystalline fatty compound comprising, at a temperature of 25° C., a liquid fraction and a solid fraction.

As illustrated in the examples shown below, the Applicant has identified a selection of pasty fatty substances which are compatible with the non-silicone elastomer according to the invention and make it possible to obtain the desired properties of texture, sensoriality and stability.

Thus, the composition of the invention comprises one or more pasty fatty substances chosen from the group consisting of (i) esters of polyol(s) and fatty acid diacid dimer, or an ester thereof (ii) hydrogenated castor oil esters, (iii) oligomeric esters of glycerol, in particular esters of diglycerol, (iv) and mixtures thereof.

Ester of Polyol(s) and Fatty Acid Diacid Dimer, or an Ester Thereof

According to a first embodiment, the composition of the invention comprises at least one pasty fatty substance chosen from esters of polyol(s) and fatty acid diacid dimer, or of one of its esters, in particular esters of diol dimer and diacid dimer, if appropriate esterified on their free alcohol or acid function(s) by acid or alcohol radicals, in particular dimer dilinoleate esters.

The fatty acid diol dimer and diacid dimer esters usable in the context of the present invention are commercially available or can be prepared conventionally. In particular, they may be of vegetable origin and may be obtained by esterification of diacid dimers with diol dimers.

According to a particular embodiment, the diol is selected from a fatty alcohol dimer, mono- or poly-glycerol, mono- or poly-C2-4 alkylene glycol, 1,4 butanediol, and pentaerythritol.

In particular, the diol is derived from the hydrogenation of a diacid dimer of at least one unsaturated fatty acid.

According to a particular embodiment, the fatty acid is an unsaturated C8 to C34 fatty acid, in particular C12 to C22, in particular C16 to C20 and more particularly C18. Among the fatty acids, we can notably mention undecenoic acid, linderic acid, myristoleic acid, palmitoleic acid, oleic acid, linoleic acid, elaidinic acid gadolenic acid, eicosapentaenoic acid, docosahexaenoic acid, erucic acid, brassidic acid, arachidonic acid, and mixtures thereof, preferably linoleic acid.

Preferably, the diacid dimer is derived from the dimerization of linoleic acid.

According to a particular embodiment, said ester is selected from esters of the following general formulas (I), (II) or (IV):

[Chem 1]

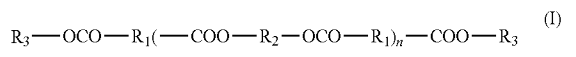

Wherein:

$COR_1CO$ represents a fatty acid diacid dimer residue, $OR_2O$ represents a fatty alcohol dimer residue, $OR_3$ represents a hydrocarbon monoalcohol residue, and n is an integer from 1 to 15, or

[Chem 2]

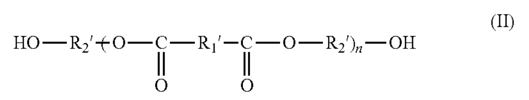

wherein:

n is an integer from 1 to 15, $COR'_1CO$ represents a fatty acid diacid dimer residue, $OR'_2O$ represents a diglyceryl residue of the following general formula (III):

[Chem 3]

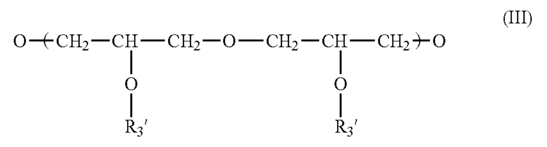

wherein:

$R'_3$ represents H or $OR'_3$ represents a fatty acid residue, or a mixture thereof, or

[Chem 4]

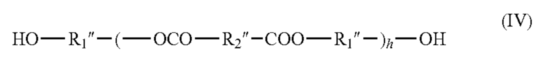

wherein:

$OR_1'O$ represents a dimer diol residue obtained by hydrogenation of a dimerdilinoleic acid, $COR_2''CO$ represents a fatty acid diacid dimer residue, and h represents an integer from 1 to 9.

Preferably, in formula (I):

$COR_1CO$ represents a dimerdilinoleate residue, $OR_2O$ represents a dimerdilinoleyl residue, and $OR_3$ represents a hydrocarbon monoalcohol residue selected from behenyl, isostearyl, phytosteryl residues and mixtures thereof.

Preferably in formula (II):

$COR_1'CO$ represents a dimerdilinoleate residue, and the fatty acid residue represented by $OR'_3$ is an isostearyl residue.

Preferably in formula (II), $COR_2''CO$ represents a dimer dilinoleate residue.

Such esters may be selected from the following INCI nomenclature:

polyglyceryl-2-isostearate/dimer dilinoleate copolymer (Hailucent ISDA from Estenity);

bis-behenyl/isostearyl/phytosteryl dimerdilinoleyl dimerdilinoleate (Plandool G from Estenity), or phytosteryl/isostearyl/stearyl/behenyl dimerdilinoleate (Plandool H or Plandool S), dimerdilinoleyl dimerdilinoleate (Lusplan DDA7 from Unipex), and mixtures thereof.

According to a particular and preferred embodiment, the composition of the invention comprises at least one pasty fatty substance of formula (I), wherein:

$COR_1CO$ represents a dimerdilinoleate residue, $OR_2O$ represents a dimerdilinoleyl residue, and $OR_3$ represents a hydrocarbon monoalcohol residue selected from behenyl, isostearyl, phytosteryl and mixtures thereof.

And we will use preferably the pasty fatty substance of INCI name: bis-behenyl/isostearyl/phytosteryl dimerdilinoleyl dimerdilinoleate (Plandool G of Estenity).

The total content of diol and fatty acid diacid dimer ester(s), or one of its esters in the composition of the invention will generally range from 0.5% to 20% by weight, in particular from 1% to 10% by weight and preferably from 2% to 5% by weight based on the total weight of said composition.

Esters of Hydrogenated Castor Oil

According to another embodiment, the composition of the invention will comprise a pasty fatty substance selected from hydrogenated castor oil esters. Examples include:

hydrogenated castor oil dimer dilinoleate, whose INCI name is Hydrogenated Castor Oil Dimer Dilinoleate, for example that marketed under the name RISOCAST-DA-L by Estenity, hydrogenated castor oil isostearate, whose INCI name is Hydrogenated Castor Oil Isostearate, for example that marketed under the name RISOCAST MIS by Estenity, and mixtures thereof.

The total content of hydrogenated castor oil ester(s) in the composition of the invention will generally range from 0.5% to 20% by weight, in particular from 1% to 10% by weight and preferably from 2% to 5% by weight based on the total weight of said composition.

Oligomeric Esters of Glycerol, Including Diglycerol Esters

According to another embodiment, the composition of the invention will comprise a pasty fatty substance selected from oligomeric esters of glycerol, especially diglycerol esters. In particular, mention may be made of adipic acid and glycerol condensates, for which some of the hydroxyl groups of the glycerols have been reacted with a mixture of fatty acids such as stearic acid, capric acid, stearic acid and isostearic acid and 12-hydroxystearic acid.

Preferably, we mention the bis-diglyceryl polyacyladipate-2 marketed under the name Softisan 649 by the company IMCD France.

The total content of oligomeric glycerol ester(s), in particular diglycerol esters, in the composition of the invention will generally be from 0.5% to 20% by weight, in particular from 1% to 10% by weight and preferably from 2% to 5% by weight relative to the total weight of the said composition.

The person skilled in the art will know how to adjust the content of pasty fatty substance in order to obtain the desired sensoriality without making it too much glossy.

According to a particular embodiment, the total content of pasty fatty substance in the composition of the invention ranges from 0.5% to 20% by weight, in particular from 1% to 10% by weight and preferably from 2% to 5% by weight based on the total weight of the composition.

Fatty Phase

According to a particular embodiment, the fatty phase of the composition also comprises at least one ingredient chosen from oils, fats distinct from the pasty fatty substance described above, in particular waxes and butters, and mixtures thereof.

By "oil" is meant a fatty substance which is not soluble in water and is liquid at 25° C. and atmospheric pressure.

According to the present invention, "fatty substance" means a compound which is solid or comprises a solid fraction at 25° C. Mention may be made in particular of butters, waxes, pasty compounds distinct from the pasty fatty substances described above, and mixtures thereof.

According to the present invention, "wax" means a compound which is solid at 25° C. and which exhibits a reversible solid/liquid state change and a melting temperature above 30° C., preferably above 45° C.

The oils and fats that can be used according to the invention can be of animal, vegetable, mineral or synthetic origin. Preferably, biobased oils and fats are used.

The following vegetable oils and fats can be used as fatty substances or vegetable oils:

"vegetable oils" such as: deodorized sunflower oil, virgin sweet almond oil, virgin rosehip oil, avocado oil, safflower oil, camelina oil, jojoba oil, borage oil, grape seed oil, argan oil, black cumin oil, pumpkin seed oil, perilla oil, castor oil and mixtures thereof, "butters" such as: Murumuru butter, Mango butter, Shea butter, Cocoa butter and Cupuaçu butter, and mixtures thereof, "vegetable waxes" such as: Carnauba wax, beeswax, candellila wax, jojoba wax, sunflower wax, rice bran wax and mixtures thereof, and mixtures thereof.

According to a particular embodiment, the composition of the invention will comprise at least one vegetable oil and at least one vegetable fat selected from a vegetable wax, a vegetable butter and mixtures thereof.

According to a particular embodiment, the composition further comprises at least one polar hydrocarbon oil.

As defined in the present invention, by "polar oil" is meant an oil whose solubility parameter at 25° C., da, is different from 0 $(J/cm^3)^{1/2}$.

In particular, the polar hydrocarbon oil(s) comprise(s) at least one alcohol function (i.e., "alcohol oil") or at least one ester function (i.e., "ester oil").

Among the "oil alcohols", we can mention in particular C10-C26, more particularly C10-C24, and preferably C12-C22, saturated or not, branched or not, more particularly monoalcohols. More particularly, the C10-C26 alcohols are fatty monoalcohols, preferably branched when they comprise at least 16 carbon atoms. As examples of fatty alcohols which can be used according to the invention, mention may be made of linear or branched fatty alcohols, of synthetic or natural origin. As particular examples of fatty alcohols that can be used as preferred, mention may be made in particular of lauric, isostearyl, oleic alcohol, 2-butyloctanol, 2-undecyl pentadecanol, 2-hexyldecyl alcohol, isocetyl alcohol, octyldodecanol and mixtures thereof.

According to an advantageous embodiment of the invention, the fatty alcohol is octyldodecanol.

Among the ester oils, we can notably mention:

- hydroxylated esters, preferably having a total carbon number ranging from 35 to 70, such as polyglycerol-2 triisostearate, isostearyl lactate, octyldodecyl hydroxystearate, diisostearyl malate, glycerine stearate; diethylene glycol diisononanoate;
- fatty acid esters, in particular with 4 to 22 carbon atoms,
- synthetic esters such as oils of formula $R_1COOR_2$ in which $R_1$ represents the residue of a linear or branched fatty acid containing from 4 to 40 carbon atoms and $R_2$ represents a hydrocarbon chain, in particular branched, containing from 4 to 40 carbon atoms, provided that $R_1+R_2$ is ≥16, such as, for example, isononyl isononanoate, ethyl 2-hexyl palmitate octyledodecyl neopentanoate, octyl-2-dodecyl stearate, isostearyl isostearate, octyl-2-dodecyl benzoate, isopropyl myristate, isopropyl palmitate, butyl stearate, hexyl laurate, 2-ethyl-hexyl palmitate, 2-hexyl-decyl laurate, 2-octyl-decyl palmitate, 2-octyldodecyl myristate, 2-diethyl-hexyl succinate;
- esters of linear fatty acids with a total carbon number of 35 to 70;
- esters of aromatic acids and alcohols with 4 to 22 atoms;
- esters of fatty alcohols or branched C24-C28 fatty acids;
- the polyesters resulting from the esterification of at least one triglyceride of hydroxylated carboxylic acid(s) with an aliphatic monocarboxylic acid and with an aliphatic dicarboxylic acid, optionally unsaturated;
- and mixtures thereof.

The composition of the invention may also comprise at least one hydrocarbon oil selected from:

- capric/caprylic triglyceride, dicaprylyl ether, dicaprylyl carbonate, coco-caprylate/caprate, triheptanoin
- linear or branched C8-C16 alkanes, in particular:
  - C8-C16 iso-alkanes (also called isoparaffins) such as isododecane, isodecane, isohexadecane, and for example oils sold under the trade names of ISOPAR® or PERMETYL®,
  - linear or branched alkanes with hydrocarbon chains in
    - C9-C17, C10-C14, such as a mixture of undecane and tridecane, marketed by BASF Care Creations under the name Cetiol® Ultimate,
    - C15-C19, such as those marketed by Seppic under the name EMOGREEN® L15,
    - C9-C12, C12-C14, such as those marketed by BIOSYNTHIS under the name VEGELIGHT® SILK (INCI name C9-12 ALKANE), VEGELIGHT® 1214LC,
  - n-dodecane (C12) and n-tetradecane (C14), notably sold by Sasol respectively under the references PARAFOL® 12-97 and PARAFOL® 14-97,
- and mixtures thereof.

According to a particular embodiment, the composition of the invention comprises oils selected from the group consisting of vegetable oils, C10-C26 alcohol oils, ester oils preferably hydroxylated, and mixtures thereof.

According to a particular and preferred embodiment, the composition of the invention comprises at least one vegetable oil and at least one polar hydrocarbon oil, in particular a C10-C26 alcohol oil, in particular octyldodecanol, and an ester oil selected from hydroxylated esters and in particular polyglycerol-2 triisostearate.

The oil alcohols may be present in the composition in a content ranging from 1 to 20%, preferably from 5 to 15%, most preferably from 8 to 12% by weight based on the total weight of the composition.

The ester oils may be present in the composition in an amount ranging from 5 to 45%, preferably from 15 to 40%, most preferably from 20 to 35 by weight based on the total weight of the composition.

The vegetable oils may be present in the composition in a content ranging from 1 to 20%, preferably from 5 to 15% and most preferably from 7 to 13% by weight relative to the total weight of the composition.

The total content of oil(s) in the composition of the invention may range, for example, from 30 to 90% by weight, in particular from 40 to 80%, preferably from 50 to 75% by weight relative to the total weight of the composition.

The total content of wax(es) in the composition of the invention may range, for example, from 1 to 25% preferably from 5 to 20% by weight, in particular from 10 to 18% by weight relative to the total weight of the composition.

The total content of butter(s) in the composition of the invention may range, for example, from 0.5 to 10% by weight, in particular from 1 to 5% by weight relative to the total weight of the composition.

The composition may be manufactured by a method consisting of preparing a mixture of the copolymer in one or more oils before its incorporation into the other ingredients of the composition. These oils may have been used as a solvent in the manufacture of the copolymer.

Other Ingredients

The composition may include other ingredients commonly used in cosmetic compositions. Such ingredients may be selected from antioxidants, fragrances, preservatives, cosmetic actives, fillers, pigments, and mixtures thereof.

The fillers and pigments can be treated with a hydrophobic agent to facilitate their dispersion in the oily or fatty phase.

Advantageously, the composition also comprises at least one filler.

Among the fillers, particular mention may be made of mineral fillers, such as alumina, silica, aluminum silicate, fumed silica, silica silylate, titanium dioxide or sericite powders.

According to a particular embodiment, the composition of the invention comprises at least one filler, in particular a mineral filler, preferably still a silica, such as that marketed under the name Sunsphere H33. Advantageously, the content of filler(s), in particular silica, in the composition of the invention will range from 0.1 to 5% by weight relative to the total weight of the composition.

Advantageously, the composition of the invention, for make-up applications, also comprises at least pigments, preferably mineral pigments.

Examples of mineral pigments include titanium dioxide; black, yellow, red and brown iron oxides; manganese violet; ultramarine blue; chromium oxide; hydrated chromium oxide; carbon black and ferric blue. Preferably, titanium dioxide and iron oxides will be used.

According to a particular embodiment, the composition of the invention further comprises pigments, in particular in a content ranging from 0.1 to 20%, in particular from 1 to 18% by weight with respect to the total weight of the composition.

The cosmetic active ingredients, preferably biobased (e.g., plant extracts), can be advantageously chosen, for example, from those having an action on skin and/or lip care, such as moisturizing agents.

According to a particular embodiment, the composition of the invention comprises:

- a content of 10 to 40% by weight of a copolymer of dilinoleic acid and propanediol crosslinked with pentymethylene diisocyanate,
- a total content of 3 to 15% by weight of pasty fatty substance(s) selected from the group consisting of (i) esters of polyol(s) and fatty acid diacid dimer, or an ester thereof, (ii) esters of hydrogenated castor oil (iii) oligomeric esters of glycerol, in particular diglycerol esters, and mixtures thereof, preferably esters of polyol(s) and fatty acid diacid dimer, or of one of its esters, and advantageously in addition
  - a total content of 50 to 80% by weight of oil(s), in particular selected from the group consisting of vegetable oils, C10-C26 alcohol oils, preferably octyldodecanol, ester oils, preferably hydroxylated, preferably polyglycerol-2-triisostearate, and mixtures thereof,
  - a total content of 10 to 20% by weight of wax(es), in particular vegetable or animal waxes, preferably carnauba wax, sunflower wax and/or beeswax and
  - a total content of 1 to 5% by weight of filler(s), in particular mineral fillers, preferably still silica, based on the total weight of the composition.

Thus, according to a particular embodiment, the composition of the invention will comprise a content of biobased compounds of at least 70%, 80%, 90%, 95%, 96%, 97%, 98%, 99%, 100% by weight based on the total weight of the composition.

Galenic

The composition according to the invention is a cosmetic composition for topical application to keratinous materials, in particular the skin and/or the lips, preferably the lips. It is in particular a skin and/or lip care and/or make-up composition.

The composition of the invention may be in the form of a lip stick, a lip balm, a gloss or a liquid lipstick, preferably a lip stick, a lip balm.

According to a preferred embodiment, the composition of the invention is a solid composition for lip care and/or make-up. In particular, it may be in the form of a balm or a stick or poured into a cup, preferably a balm or a stick.

Cosmetic Method

The invention also relates to a cosmetic method for skin and/or lip care and/or make-up, comprising at least the application to the skin and/or lips of a composition according to the invention.

The combination of a non-silicone elastomer and a pasty fatty substance as described above, preferably biobased, makes it possible to obtain a homogeneous composition with a very high natural origin and with a sought-after cosmetic appeal: melting, comfort, softness, gummy sensation with a luminous matte make-up finish, a gummed and homogeneous effect on keratinous materials and in particular the lips Thus, the cosmetic method of the invention is intended in particular to obtain a comfortable matte deposit on the lips.

The invention will be illustrated by the following non-limiting examples. Percentages (%) are expressed as weight percent based on the total weight of the composition unless otherwise indicated.

EXAMPLES

Example 1: Selection of Pasty Fatty Substances

Different pasty fatty substances are tested, in terms of compatibility, sensoriality and stability (at T=24 h and T=1 week), in a simple formula containing:

TABLE 1

| Ingredient | % by weight |
|---|---|
| Polyglycerol-2 triisostearate | 65.00 |
| Triheptanoin (and) Coco-Caprylate/Caprate (and) Dilinoleic Acid/Butanediol Copolymer (and) Castor Oil/IPDI Copolymer Elastomer (GRANSENSE TC-21X-C de Grant Industries Inc.) Non-silicone elastomer according to the invention | 30.00 |
| Pasty fatty substance (to be tested) | 5.00 |

The ingredients are mixed and stirred for 10 minutes in a bain-marie 80° C. at 600 rpm.

The following criteria are evaluated:

- compatibility: the compatibility of the pasty fatty substance with the non-silicone elastomer and the oil according to the invention is evaluated at heat (80° C.) after mixing and stirring;
- stability after 24 hours (T24 h): the composition is evaluated after 24 hours, by observing sedimentation, appearance and dispersion;
- sensoriality (touch) after 24 hours: the texture of the composition is evaluated after 24 hours to the touch and the appearance and sensoriality of the film when applied to the lips;
- stability after 1 week (room temperature, at 50° C. and at TALT: alternating temperature at −5° C. and 40° C.): the stability of the composition is evaluated after 1 week under different conditions.

The results of the evaluation are presented in the following Table 2:

TABLE 2

| Commercial reference | INCI NAME | Natural origin | COMPATIBILITY | Stability at T24 h | Touch at T24 h | Stability TA 1 week | Stability T50° C. 1 week | Stability TALT 1 week |
|---|---|---|---|---|---|---|---|---|
| FLORAESTER 30 (comparative) | Jojoba esters | 100% | +++ | ++ | Not measured | + | ++ | ++ |
| FLORAESTER 70 (comparative) | Jojoba esters | 100% | +++ | +/− Appearance: pasty and crystallized | ++ | +/− Appearance: pasty and crystallized | +/− Appearance: pasty and crystallized | +/− Appearance: pasty and crystallized |
| SOFTISAN 378 (comparative) | Caprylic/capric/myristic/stearic triglyceride | 100% | +++ | ++ | Not measured | ++ | ++ | ++ |
| HAILUCENTISDA (invention) | Polyglyceryl-2 isostearate/dimer dilinoleate copolymer | 100% | +++ | +++ | ++ | ++ | ++ | ++ |
| LUSPLAN DDA7 (invention) | Dimer dilinoleyl dimer dilinoleate | 100% | +++ | +++ | ++ | ++ | ++ | ++ |
| PLANDOOL G (invention) | Bis-behenyl/isostearyl/phytosteryl dimer dilinoleyl dimer dilinoleate | 100% | +++ | +++ | +++ | ++ | ++ | ++ |
| RISOCAST DAL (invention) | Hydrogenated castor oil dimer dilinoleate | 100% | +++ | +++ | ++ | +++ | ++ | +++ |
| RISOCAST MIS (invention) | Hydrogenated castor oil isostearate | 97% | +++ | +++ | ++ | +++ | ++ | +++ |
| SOFTISAN 649 (invention) | Bis diglyceryl polyacyladipate-2 | 85% | +++ | +++ | ++ | ++ | ++ | ++ |

compatibility:
- ++=good hot dispersion stability at T24 h:
- ++=no sedimentation, turbid liquid appearance and homogeneous dispersion
- ++=no sedimentation but inhomogeneous dispersion (small homogeneous points)

stability after 1 week:
- +++=no sedimentation, turbid liquid appearance and homogeneous dispersion
- ++=sedimentation, turbid liquid appearance and homogeneous dispersion
- +=sedimentation and inhomogeneous dispersion (small homogeneous points)

sensoriality:
- +++=soft, slippery, substantive, comfort
- ++=soft, slippery, substantive, a little clingy at the end and/or medium shine These results show that pasty fatty substances selected from the group consisting of
- (i) esters of polyol(s) and fatty acid diacid dimer, or an ester thereof
- (ii) hydrogenated castor oil esters
- (iii) oligomeric esters of glycerol, especially diglycerol esters, compared to pasty fatty substances such as jojoba esters (Floraesters) or caprylic/capric/myristic/stearic triglycerides (Softisan 378), make it possible to obtain the desired properties of texture, sensoriality and stability.

Example 2: Tinted Lip Balm

2-1 Tinted Lip Balm

TABLE 3

| Phase | Ingredient | % by weight |
|---|---|---|
| A1 | Polyglycerol-2 triisostearate | Qsp100 |
| A1 | Vegetable waxes | 10.00 |
| A1 | Octyldodecanol | 10.00 |
| A1 | Vegetable oils | 30.00 |
| A1 | bis- behenyl/isostearyl/phytosteryl dimerdilinoleate (PLANDOOL G from Estenity) Pasty fatty substance according to the invention | 3.00 |
| A2 | Trilepton (and) Coco-Caprylate/Caprate (and) Dilinoleic Acid/Butanediol Copolymer (and) Castor Oil/IPDI Copolymer Elastomer (GRANSENSE TC-21X-C de Grant Industries Inc.) | 20.00 |

TABLE 3-continued

| Phase | Ingredient | % by weight |
|---|---|---|
| | Non-silicone elastomer according to the invention | |
| B | Pigments (red, yellow and black iron oxides) | 1.60 |
| C | Silica (Sunsphere H33) | 1.00 |

The composition is prepared according to the following protocol:

- the ingredients of phase A1 are weighed and melted in a water bath at 95° C., then homogenized under Rayneri for 15 minutes;
- the non-silicone elastomer according to the invention (A2) is added and stirred for 15 minutes;
- the pigments (B) are added and mixed for 15 minutes under Rayneri;
- the silica (C) is then dispersed, stirred for 5 minutes and passed through the Turrax to obtain a homogeneous composition
- the composition is then hot poured into a tool to obtain a stick (e.g., silicone pacifier, metal mold or cup) or directly into the final packaging (bottle).

The composition obtained is presented in the form of a homogeneous, soft, mellow stick, of gummy texture, coating, slightly covering, with a weightless effect on application, and without transfer, with a gummy matte finish and slightly colored (bitten lips effect) on the lips.

2-2 Lip Balm

TABLE 4

| Phase | Ingredient | % by weight |
|---|---|---|
| A1 | Polyglycerol-2 triisostearate | Qsp100 |
| A1 | Vegetable waxes | 10.00 |
| A1 | Octyldodecanol | 10.00 |
| A1 | Vegetable oils | 40.00 |
| A1 | Hydrogenated castor oil isostearate (RISOCAST MIS) | 5.00 |
| | Pasty fatty substance according to the invention | |
| A2 | Triheptanoin (and) Coco-caprylate/caprate (and) Dilinoleic Acid/Butanediol Copolymer (and) Castor Oil/IPDI Copolymer Elastomer (and) Butyrospermum Parkii (Shea) Butter). (GRANSENSE TC-21X-SBC de Grant Industries Inc.) | 20.00 |
| | Non-silicone elastomer according to the invention | |
| B | Pigments (red, yellow and black iron oxides) | 1.60 |
| C | Silica (Sunsphere H33) | 1.00 |

The composition is prepare according to the method described in Example 2-1.

The composition has a gummy, slightly covering texture for a natural gummy matte finish on the lips.

2-3 Lip Balm

TABLE 5

| Phase | Ingredient | % by weight |
|---|---|---|
| A1 | Polyglycerol-2 triisostearate | Qsp100 |
| A1 | Vegetable waxes | 10.00 |
| A1 | Octyldodecanol | 10.00 |
| A1 | Vegetable oils | 50.00 |
| A1 | bis-diglyceryl polyacyladipate-2 (Softisan 649) | 10.00 |
| | Pasty fatty substance according to the invention | |
| A2 | Coco-Caprylate/Caprate (and) Triheptanoin (and) C9-12 Alkane (and) Dilinoleic Acid/Butanediol Copolymer (and) Castor Oil/IPDI Copolymer Elastomer (GRANSENSE TC-18-X-C de Grant Industries Inc.) | 15.00 |

TABLE 5-continued

| Phase | Ingredient | % by weight |
|---|---|---|
| | Non-silicone elastomer according to the invention | |
| B | Pigments (red, yellow and black iron oxides) | 1.60 |
| C | Silica (Sunsphere H33) | 1.00 |

The composition is prepared according to the method described in Example 2-1.

The composition has a melting, gummy, slightly covering texture, for a matte and natural finish on the lips.

The invention claimed is:

1. A cosmetic composition comprising, in a physiologically acceptable medium:
 a cross-linked polyurethane elastomer gel comprising
  a single crosslinked polyurethane elastomer (copolymer) or a mixture of at least two crosslinked polyurethane elastomers (copolymers), said copolymer or said mixture of copolymers being obtained from a prepolymer having at least two hydroxyl groups and a (poly)isocyanate and at least one solvent, at least one polyol and a diisocyanate, and
  one or more pasty fatty substances selected from the group consisting of:
   (i) esters of polyol(s) and fatty acid diacid dimer, or an ester thereof,
   (ii) hydrogenated castor oil esters,
   (iii) oligomeric esters of glycerol,
   (iv) and mixtures thereof
wherein the prepolymer having at least two hydroxyl groups is a copolymer of a C12-C18 fatty acid dimer, and a polyol selected from the group consisting of an aliphatic diol having 2 to 8 carbon atoms, and wherein the (poly)isocyanate is a diisocyanate.

2. The cosmetic composition according to claim 1, which is in a solid form.

3. The cosmetic composition according to claim 1, wherein the crosslinked polyurethane elastomer (copolymer) is a single crosslinked polyurethane elastomer (copolymer) or a mixture of at least two crosslinked polyurethane elastomers (copolymers), said copolymer or said mixture of copolymers being obtained from a prepolymer from a carboxylic acid dimer or trimer having at least two hydroxyl groups and a (poly)isocyanate and at least one solvent, at least one polyol and a diisocyanate, and the oligomeric esters of glycerol (iii) are esters of diglycerol, wherein the prepolymer having at least two hydroxyl groups is a copolymer of a C12-C18 fatty acid dimer, and a polyol selected from the group consisting of an aliphatic diol having 2 to 8 carbon atoms, and wherein the (poly)isocyanate is a diisocyanate.

4. The composition according to claim 1, wherein it comprises a copolymer obtained from a prepolymer of dilinoleic acid and propanediol or butanediol, and 1,5-pentamethylene diisocyanate.

5. The composition according to claim 1, wherein it comprises a mixture of two copolymers, said mixture being obtained from prepolymers of dilinoleic acid/polyols and isophorone diisocyanate, the two polyols being butanediol and castor oil.

6. The cosmetic composition according to claim 1, wherein the polyurethane elastomer gel comprises at least one solvent selected from the group consisting of triglycerides of vegetable origin, $C_9$-$C_{22}$ alkanes, naturally occurring esters, and mixtures thereof.

7. The cosmetic composition according to claim 1, wherein the said polyurethane elastomer gel comprising the said copolymer or the said mixture of at least two copolymers is present in the composition in a total dry (active) matter content ranging from 0.5% to 5% by weight, relative to the total weight of the composition.

8. The cosmetic composition according to claim 1, wherein the pasty fatty substance is a linoleic acid diol dimer diacid ester.

9. The cosmetic composition of claim 1, wherein the ester of polyol(s) and fatty acid diacid dimer, or an ester thereof is of formula (I)

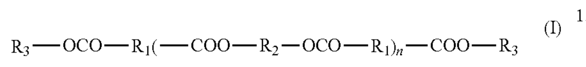

wherein $COR_1CO$ represents a dimerdilinoleate residue, $OR_2O$ represents a dimerdilinoleyl residue, and $OR_3$ represents a hydrocarbon monohydric alcohol residue selected from behenyl, isostearyl, phytosteryl, and mixtures thereof, and n is an integer from 1 to 15.

10. The cosmetic composition according to claim 1, wherein the total content of pasty fatty substance ranges from 0.5% to 20% by weight, based on the total weight of the composition.

11. The cosmetic composition according to claim 1, wherein it further comprises at least one ingredient chosen from oils, waxes, butters, and mixtures thereof.

12. The composition according to claim 11, wherein the oils are selected from the group consisting of vegetable oils, $C_{10}$-$C_{26}$ alcohol oils, ester oils, and mixtures thereof.

13. The composition according to claim 1, wherein it further comprises at least one filler.

14. The composition according to claim 1, wherein it comprises at least 70% by weight of biobased ingredients.

15. The cosmetic composition according to claim 1, wherein it additionally comprises pigments.

16. The cosmetic composition according to claim 1, wherein it is a lip stick, a lip balm, a gloss or a liquid lipstick.

17. Cosmetic method for caring for and/or making up keratinous materials, wherein it comprises the application to the said keratinous materials of a composition as defined in claim 1.

18. The composition according to claim 1, wherein it comprises at least 90% by weight of biobased ingredients.

19. The composition according to claim 1, wherein it comprises at least 95% by weight of biobased ingredients.

* * * * *